(12) United States Patent
Dalal et al.

(10) Patent No.: US 9,430,614 B2
(45) Date of Patent: *Aug. 30, 2016

(54) INTERVENTIONAL INFORMATION BROKERING MEDICAL TRACKING INTERFACE

(71) Applicant: KONINKLIJKE PHILIPS N.V., Eindhoven (NL)

(72) Inventors: Sandeep M. Dalal, Cortlandt Manor, NY (US); Xin Liu, Scarsdale, NY (US); Christopher Stephen Hall, Kirkland, WA (US)

(73) Assignee: Koninklijke Philips N.V., Eindhoven (NL)

( * ) Notice: Subject to any disclaimer, the term of this patent is extended or adjusted under 35 U.S.C. 154(b) by 4 days.

This patent is subject to a terminal disclaimer.

(21) Appl. No.: 14/397,872

(22) PCT Filed: May 9, 2013

(86) PCT No.: PCT/IB2013/053751
§ 371 (c)(1),
(2) Date: Oct. 30, 2014

(87) PCT Pub. No.: WO2013/168117
PCT Pub. Date: Nov. 14, 2013

(65) Prior Publication Data
US 2015/0123769 A1    May 7, 2015

Related U.S. Application Data

(60) Provisional application No. 61/644,489, filed on May 9, 2012.

(51) Int. Cl.
*G06F 19/00* (2011.01)
*G11B 27/00* (2006.01)
(Continued)

(52) U.S. Cl.
CPC ............ *G06F 19/3406* (2013.01); *A61B 5/06* (2013.01); *G11B 27/34* (2013.01); *A61B 5/00* (2013.01)

(58) Field of Classification Search
CPC ............ G06F 19/3406; A61B 19/50; A61B 2019/507; A61B 19/5244; A61B 19/54; A61B 5/0422; A61B 5/0538; A61B 5/061; A61B 1/0008; A61B 5/06; A61B 10/0283; A61B 5/00; G11B 27/34
USPC ......... 340/8.1; 600/509, 117, 424, 407, 410, 600/429

See application file for complete search history.

(56) References Cited

U.S. PATENT DOCUMENTS

| | | | |
|---|---|---|---|
| 7,901,348 B2 * | 3/2011 | Soper .................. | A61B 1/0008 600/117 |
| 2012/0059248 A1 * | 3/2012 | Holsing ............... | A61B 1/2676 600/424 |
| 2015/0379710 A1 * | 12/2015 | Holsing ................ | G06T 7/0012 382/131 |

OTHER PUBLICATIONS

Vaccarrella et al, "Modular Multiple Sensors Information Management for Computer-Integrated Surgery", The International Journal of Medical Robitcs and Computer Assisted Surgery, Mar. 8, 2012, XP002715218, pp. 253-260.

(Continued)

*Primary Examiner* — Ali Neyzari (57) ABSTRACT

A method, system, and program product are provided for providing a medical tracking interface. The method comprises the steps of: receiving tracking data from at least one tracking tool in any one of a plurality of data formats; converting the tracking data to a uniform data format; and outputting the tracking data in the uniform data format to an IGI application.

14 Claims, 6 Drawing Sheets

(51) Int. Cl.
*A61B 5/06* (2006.01)
*G11B 27/34* (2006.01)
*A61B 5/00* (2006.01)

(56) References Cited

OTHER PUBLICATIONS

Uneri et al, "Trek: An Integrated System Architecture for Intraoperative Cone-Beam CT-Guided Surgery", International Journal of Computer Assisted Radiology and Surgery, vol. 7, No. 1, Jul. 9, 2011, XP109995058, pp. 159-173.

Birkfellner et al, "Calibration of Tracking Systems in a Surgical Environment", IEEE Transactions on Medical Imaging, vol. 17, No. 5, Oct. 1, 1998, XP011035767, pp. 737-742.

Lu et al, "Integration of the Image-Guided Surgery Toolkit (IGSTK) Into the Medical Imaging Interaction Toolkit (MITK)", Journal of Digital Imaging, vol. 25, No. 6, Apr. 26, 2012, XP035134623, pp. 729-737.

\* cited by examiner

INTERVENTIONAL INFORMATION BROKERING MEDICAL TRACKING INTERFACE

CROSS-REFERENCE TO PRIOR APPLICATIONS

This application is the U.S. National Phase application under 35 U.S.C. §371 of International Application Serial No. PCT/IB2013/053751, filed on May 9, 2013, which claims the benefit of U.S. Application Ser. No. 61/644,489, filed on May 9, 2012. These applications are hereby incorporated by reference herein.

FIELD OF THE INVENTION

The invention relates to the field of medical imaging and more particularly to a method, system and computer program product for providing a medical tracking interface MTI for interventional information brokering for more than one imaging and/or tracking system.

BACKGROUND

Communication of real-time data between image acquisition equipment, minimally invasive sensing, therapy delivery and monitoring devices, and software applications executing on workstations is a common feature in medical image-guided intervention (IGI) applications. Surgical tools or minimally invasive instruments e.g., needles, catheters, guidewires, imaging probes inserted into the body, and the like can be located relative to the patient's body by using tracking systems that can determine the position and orientation of interventional instruments, and possibly the entire instrument shape and communicate these measurements in real-time to external devices. These systems use a variety of intrinsic detection technologies, e,g, optical camera-based detection of markers embedded on instruments, electromagnetic sensing of miniaturized sensors embedded on instruments placed in an electromagnetic field, optical shape sensing using Fiber Bragg Grating (FBG) or Raleigh scatter concepts, and other technologies. Manufacturers of tracking systems may use different data communication protocols and proprietary interfaces, which slow down the integration of IGI applications in clinical practice. IGI applications have to interface individually with each manufacturer's equipment to acquire tracking information, which increases the re-engineering hurdle and hinders interoperability if multiple tracking systems using one or more intrinsic technologies are simultaneously used in the same intervention. Errors and redundancy may be introduced without a standard interface to IGI applications.

Software applications exist that provide an interface to tracking hardware and include other functionality, such as read/display medical images, point-based registration, etc. However, these applications do not combine or coordinate information from multiple tracking systems.

SUMMARY

A method, system and program product are provided for providing a medical tracking interface (MTI) acting as an information broker that communicates with a variety of medical tracking systems for medical interventions.

According to one aspect of the present invention, a method is provided for providing a medical tracking interface. The method comprises the steps of: receiving data from at least one tracking device in any one of a plurality of formats, converting the data to a uniform format, and outputting the data in the uniform format.

According to one embodiment, the uniform format to which the tracking data is converted is a uniform spatial coordinate system. According to various embodiments, the uniform spatial coordinate system may be: positions encoded using three dimensional cartesian coordinates, orientations encoded using quaternions or Euler angles, and position and orientations encoded using a transform matrix.

According to one embodiment the uniform format comprises spatial alignment of each of the at least one tracking devices to a uniform external reference frame. A user touches each tracking device to a plurality of reference features at known locations in an external reference frame. The tracking system measures the reference feature locations in the tracking device coordinates and sends them to the MTI. The MTI calculates a registration matrix from the reference feature measurements and the corresponding tracking system coordinates. Using the registration matrix, the MTI converts or aligns the tracking device data to the external reference frame coordinates. The MTI outputs the tracking data in the external reference frame coordinates.

According to one embodiment, the method of providing a medical tracking interface further comprises the step of sharing imaging data associated with tracking coordinates from one tracking system to tracked interventional instruments associated with another tracking system using the registration matrix to align the tracking coordinates of the imaging data to the tracking system receiving the imaging data.

According to one embodiment, the uniform format comprises spatial alignment of each of the at least one tracking devices to an external reference frame, and further comprises the steps of: touching at least one tracking device to a plurality of reference features at known locations in the external reference frame; measuring the reference feature locations in the tracking device coordinates; calculating a registration matrix from the reference feature measurements; using the registration matrix to align the tracking device data to the external reference frame; outputting the tracking data in external reference frame coordinates; determining at least one common reference frame for the at least one tracking device and a dependent tracking device; calculating a registration matrix for the dependent tracking device using the registration matrix for the at least one tracking device and the common reference frame; using the registration matrix to align the dependent tracking device data to the external reference frame coordinates; and outputting the tracking data for the dependent tracking device in the external reference frame coordinates.

According to one embodiment, the method for providing a medical tracking interface further comprises detecting errors in one of the at least one tracking devices; and notifying each dependent tracking device to determine and use new registration matrices.

According to one embodiment, the uniform format comprises a uniform temporal reference frame. In one embodiment, at least one tracking device provides data at any one of a plurality of streaming rates, and the data stream is buffered and output at a uniform streaming rate. In another embodiment, more than one tracking device provides data at more than one streaming rate and the data streams are synchronized.

According to another embodiment, the uniform format comprises a uniform temporal frame where the measurements in the data stream include timestamps with a uniform reference frame. A latency detection module measures latency for each of at least one tracking device, and converts a tracking device timestamp to a uniform interface timestamp using the measured latency.

According to one embodiment, the method of providing a medical tracking interface further comprises synchronizing the tracking data with physiological monitoring data, e.g. ECG, heart rate, respiratory phase, etc.

According to one embodiment, temporal synchronization is provided by touching fiducials or other features that are identifiable in an image stream. The touching is detected via analysis of the imaging data stream, from which the timestamp of the imaging stream is captured. Then, the timestamp from the imaging data stream are synchronized with a uniform time reference from the MTI.

According to another aspect of the present invention, a medical tracking interface (MTI) is provided. The MTI comprises: a processor, a memory operably connected to the processor, and a program of instruction stored on the memory and executed by the processor to convert data from any of a plurality of formats to a uniform format and output the data in the uniform format.

According to one embodiment, the program of instruction converts the data to a uniform format comprises a uniform spatial coordinate system.

According to one embodiment, the program of instruction performs spatial alignment of each of the at least one tracking devices to a uniform external coordinate system by calculating and using a registration matrix.

According to one embodiment, the MTI further comprises a multiplexer, wherein the multiplexer buffers and temporally aligns the data streams of each of the at least one tracking devices to a medical tracking interface reference.

According to one embodiment, the MTI further comprises a reference clock, wherein the program of instruction determines and compensates for latency for each of the at least one tracking devices by requesting and receiving a signal from the tracking device with a tracking device time stamp, recording a medical tracking interface time stamp upon requesting and receiving the signal and associating the tracking device time stamp with the average of the medical tracking interface time stamps.

According to one embodiment, the program of instruction detects touching at least one tracking device to a plurality of reference features at known locations in an external reference frame coordinate system, measures the reference feature locations in the tracking device coordinates, calculates a registration matrix from the reference feature measurements, using the registration matrix, aligns the tracking device data to the external reference frame coordinates, and outputs the tracking data in the external reference frame coordinates.

According to one embodiment, the program of instruction further: determines at least one common reference frame for the at least one tracking device and a dependent tracking device, calculates a registration matrix for the dependent tracking device using the registration matrix for the at least one tracking device and the common reference frame, using the registration matrix for the dependent tracking device, aligns the dependent tracking device data to the external reference frame coordinates, and outputs the tracking data for the dependent tracking device in the external reference frame coordinates.

According to one embodiment, the program of instruction further: detects errors in one of the at least one tracking devices, and notifies each dependent tracking device to determine and use new registration matrices.

According to one embodiment, the MTI comprises a clock that provides a uniform temporal reference frame timestamp and the program of instruction detects a touching of at least one tracking device to a reference feature that is identifiable in an imaging data stream and capturing the uniform reference frame timestamp for the touching, detecting the touching in the imaging data stream via analysis of the imaging data stream and capturing a timestamp of the imaging stream, and synchronizing the imaging stream timestamp with corresponding timestamp from the uniform time reference frame.

According to another aspect of the invention, a computer program product for providing a medical tracking interface is provided. The program product comprises a computer readable storage device having encoded thereon a computer executable program of instruction. The program of instruction comprises: program instructions for converting the data to a uniform format, and program instructions for outputting the data in the uniform format.

BRIEF DESCRIPTION OF THE DRAWINGS

The features and advantages of the invention will be more clearly understood from the following detailed description of the preferred embodiments when read in connection with the accompanying drawing. Included in the drawing are the following figures.

DETAILED DESCRIPTION

The present invention provides a method, system, and computer program product for providing a medical tracking interface (MTI) that communicates with one or more medical tracking systems, receiving tracking data from the tracking systems, converting the data to a uniform format, and outputting the data in real time to IGI applications on host computers. The MTI can receive tracking data in any of a variety of formats and structures and convert the data into a uniform format. The MTI may provide data in a uniform spatial coordinate format, such as Cartesian coordinates (x,y,z), rotational axes and angles using quaternion (u,v,w,s), rotation using three Euler angles, or transformation matrices for positional or rotational coordinates. The MTI may also align coordinates for a plurality of tracking devices, patient coordinates, coordinates from other equipment, and coordinates for pre-operative or intra-operative imaging. Additionally or alternatively, the MTI may align the data streams of a plurality of tracking devices, coordinates from patient trackers or other equipment, and intra-operative imaging devices to provide a uniform temporal format.

The conversion process may be performed by a processor, such as a general purpose computer, executing a program of instructions for converting tracking data to a uniform format and outputting data streams in the uniform format in real time. The conversion program of instructions may call various modules for converting the coordinate format, calculating and applying registration transforms, special synchronization, temporal synchronization, latency determination, error detection and multiplexing. The modules may be software code, hardware devices or combinations thereof.

Figure 1:
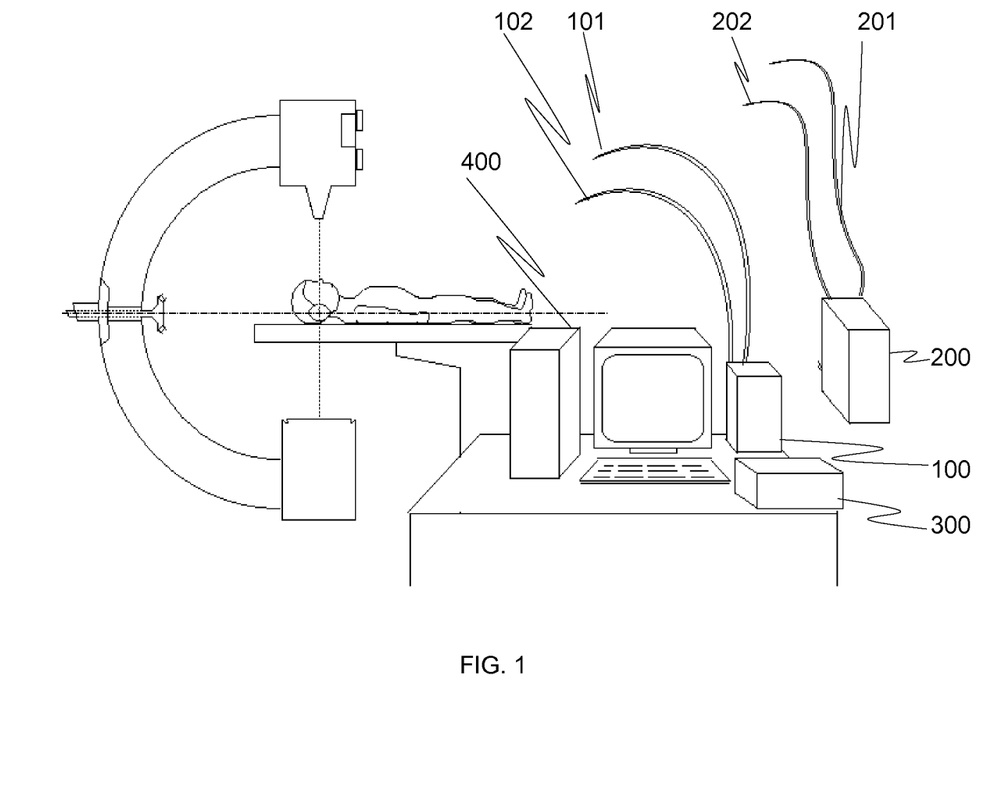
FIG. 1 is an isometric view of a system for providing a medical tracking interface according to an embodiment of the present invention.

FIG. 1 shows a system for providing a medical tracking interface according to an embodiment of the present invention. In the illustrated embodiment, the system comprises: two tracking systems 100, 200. The tracking systems may be electromagnetic, optical, optical shape sensing, or any other suitable tracking technology. Each tracking system is connected to a tracking tool 101, 102, 201, 202, such as a catheter, needle, camera, or any other diagnostic or therapeutic tool that may be tracked during an intervention. The tracking systems 100, 200 are used for tracking the location of the tools 101, 102, 201, 202 during a surgical procedure, such as a catheter-based intervention.

The tracking systems 100, 200 comprise a processor operably connected with the tools that processes signals such as voltage measurements from an electromagnetic sensor in an electromagnetic tracking system or reflected wavelengths in an optical shape sensing tracking system, or any other tracking signal. The signals are processed and a stream of tracking data is output, in the form of location coordinates for the sensors which are embedded or affixed on surgical tools or location coordinates of desired points on the instrument e.g. the tip, or the shape of the instrument, etc. The tracking system may further comprise a memory operably connected with the processor with program instructions for converting the measurement signals into location data.

A medical tracking interface (MTI) 300 receives the tracking data from the tracking systems 100, 200, converts the tracking data to a uniform format, and outputs the tracking data in the uniform format. A computer 400 comprising a processor 410 running an image-guided intervention (IGI) application 422 (FIG. 2) that is stored on a memory 420 receives the output tracking data through an input/output connection 440 and super-imposes the tool location on an anatomic image in real time, and presents the image with tool location on a display 430. The processor 410, memory 420, display 430, and Input/Output connector 440 may be interconnected through a bus 450, for example.

Figure 2:
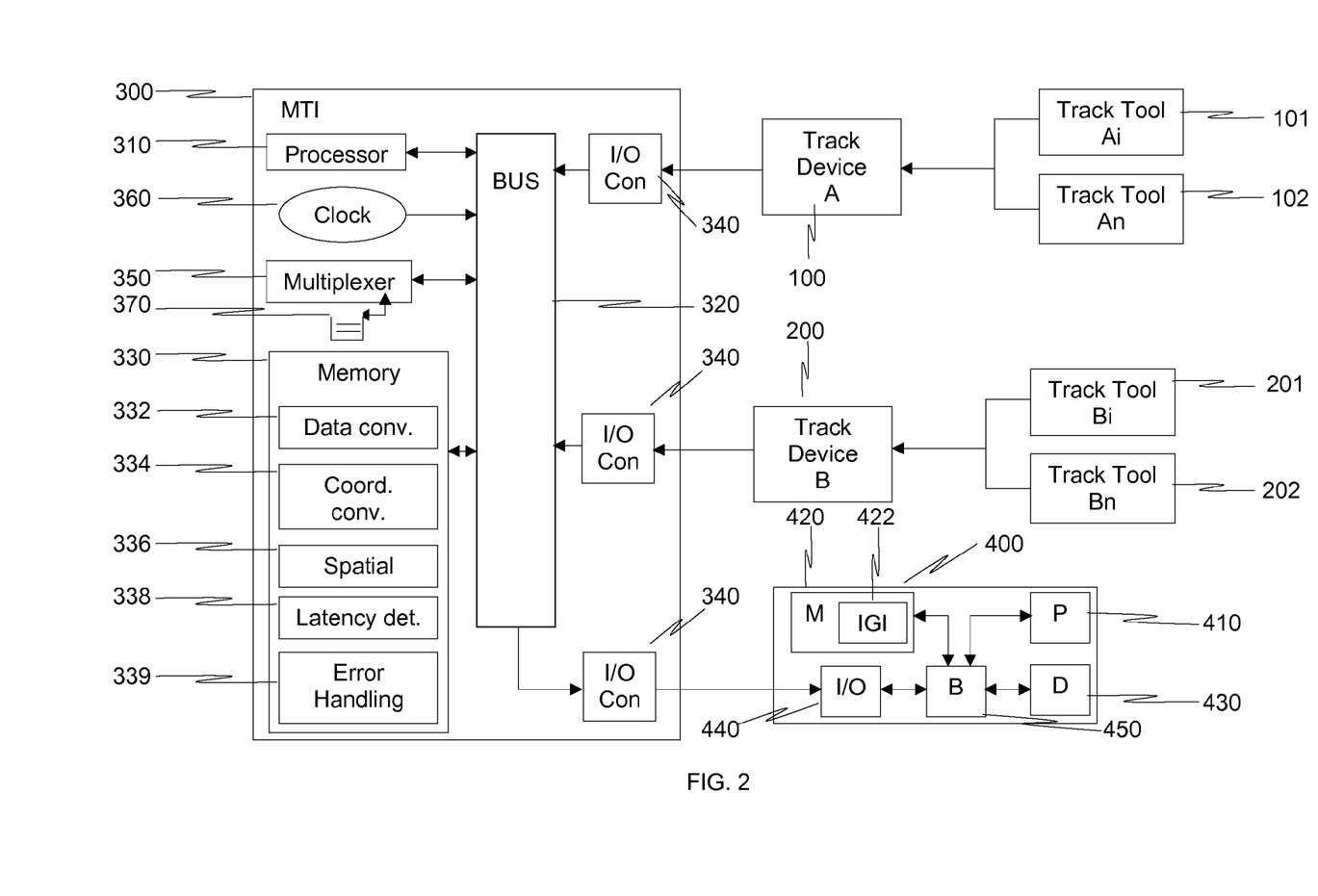
FIG. 2 is a block diagram of a system for providing a medical tracking interface according to an embodiment of the present invention.

FIG. 2 is a block diagram of the MTI 300 according to an embodiment of the present invention. The MTI 300 comprises a processor 310, a memory 330 operably connected to the processor such as by a system bus 320 for example, and input/output (I/O) connectors 340 that operably connect the tracking systems 100, 200 to the processor 310. The processor 310 may be may be any device capable of executing program instructions, such as one or more microprocessors. Moreover, the processor 310 may be embodied in a general purpose computer.

The memory 330 may be any volatile or non-volatile memory device suitable for storing data and program instructions, such as a removable disc, a hard drive, a CD, a Random Access Memory (RAM), a Read Only Memory (ROM), or the like. Moreover, the memory 330 may comprise one or more memory devices.

The I/O connectors 340 may be any hardware that operably connects the MTI to the tracking systems 100, 200 or the computer 400 running IGI applications. The I/O connectors may include, but are not limited to RS232 serial interface, Ethernet, and USB ports.

The MTI further comprises a data conversion program of instruction 332 stored on the memory 330 and executed by the processor 310 to convert tracking data from the tracking systems 100, 200 into a uniform format. The data conversion program of instruction 332 may include modules or units for one or more data conversion functions. The data conversion function may include: convert coordinate formats from any of a plurality of formats into a uniform format, calculate and apply registration transforms, align coordinates frames of one or more tracking systems to a universal or world reference frame, broker coordinate frame dependencies, temporally synchronize a plurality of tracking data streams, detect and correct for tracking data latency, and detect errors and provide notification and/or fail-over. Each module or unit may be incorporated in the data conversion program of instruction 332, be a separate application callable by the data conversion program of instruction 332, or be a separate hardware unit such as a logic circuit accessible by the data conversion program of instruction 332.

In the illustrated embodiment of FIG. 2, a coordinate formatting module 334, a spatial synchronization module 336, a latency detection module 338, and an error handling module 339 are separate, callable applications stored on memory 330. Also, a multiplexer 350 is a separate hardware unit in the MTI 300 accessible by the data conversion program of instruction 332 through the processor 310. However, it should be understood that different embodiments are contemplated within the scope of the invention where fewer than all of the illustrated data conversion modules are provided or where additional data conversion modules are provided. Also, the various data conversion modules may alternatively be all software application, all hardware, or any combination of software and hardware.

Figure 3:
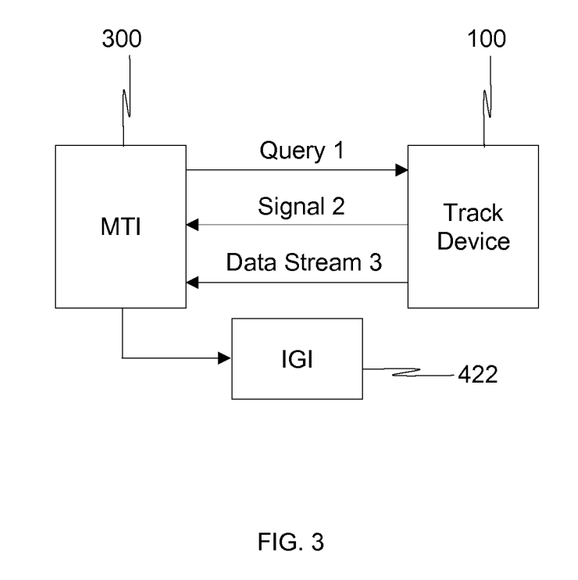
FIG. 3 shows a method for providing a medical tracking interface according to an embodiment of the present invention.

According to one embodiment, when a tracking system 100, 200 is connected to the MTI 300, it sends a signal 2 indicating its availability, as shown in FIG. 3. This signal may be sent automatically by the tracking system 100, 200 or may be sent in response to a query 1 by the MTI 300. The signal may include identification of the characteristics of the tracking data such as the sample rate of the measurements by the tracking system, the coordinate format for the tracking system, a time stamp from the tracking system, and reference frames known to the tracking system.

Alternatively, characteristics of the tracking system may be input to the data conversion program of instruction 332 by a user through an input device, such as a keyboard or mouse.

The tracking system 100 then sends a tracking data stream 3 to the MTI 300. The MTI converts the tracking data stream to a uniform format and sends a uniform data stream 4 to the IGI 422.

As depicted in FIG. 2, the MTI 300 includes hardware that inputs data from one or more tracking systems 100, 200 and outputs this data in real-time to IGI applications 422 on host computers 400. The tracking systems 100, 200 connect one or more sensors embedded on devices or instruments (i.e., tools) 101, 102, 201, 202 that are tracked during an interventional procedure using electromagnetic fields, shape sensing, or other tracking techniques. The tracking system computes the position and orientation of the sensors in a reference space and outputs measurement data coordinates, which may include x, y, z (Cartesian) coordinates, angles, or combinations for each sensor. This information is acquired many times per second (frame or sample rate) and makes it possible to track the motion of the tool.

There may be several modules in the MTI 300. Following is a description of exemplary modules of the MTI 300.

A coordinate conversion module 334 converts tracking data from any of a variety of coordinate formats into a uniform spatial coordinate format. For example, various tracking systems may provide tracking data for position and orientation of a tool in any of multiple formats. Some common formats include: position data using 3D spatial coordinates (x, y, z), rotation axis and angles encoded using quaternion (u, v, w, s), rotation encoded using three Euler angles, and position and rotation encoded using a 3×4 or 4×4 transform matrix. The coordinate conversion unit can accept data in any combination of formats and convert the data to a uniform, preferred format, as needed. The preferred format mat be selected and input by a user through an input device such as a keyboard or mouse. Alternatively, the preferred format may be defined by the IGI application 422 and provided to the MTI 300 by a communication signal. The format of the data stream from the tracking systems 100, 200 may be identified by the MTI 300 based on the coordinate characteristics, or the user may input the coordinate format for each tracking system, or the tracking system 100, 200 may indicate the coordinate format of its data stream in a communication signal sent to the MTI 300.

Figure 4:
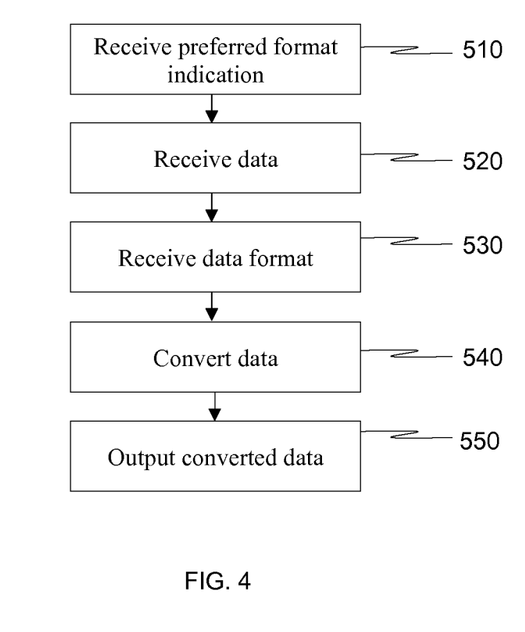
FIG. 4 is a flow diagram of a system for providing a medical tracking interface according to an embodiment of the present invention.

FIG. 4 is a flow diagram of the coordinate conversion module 332. The coordinate conversion module receives an indication of the preferred output coordinate format (Step 510). This indication may be from the IGI or from a user input. The coordinate conversion module 332 receives the tracking data stream (Step 520). The coordinate conversion module 332 identifies the coordinate format of the data stream (Step 530). The coordinate format may be identified by characteristics of the data, from a signal 2 sent by the tracking system 100, or from a user input. The coordinate format of the data stream may be identified before or after the data stream is received, depending on how it is identified. The coordinate conversion module 332 converts the data from the coordinate format of the data stream 3 to the preferred output coordinate format using conversion formulas known in the art (Step 540). The coordinate conversion module 332 outputs the converted data (Step 550).

A spatial synchronization module 336 may also be provided in the MTI 300. Different tracking systems have different coordinate frames. Therefore, an instrument tracked in a first coordinate frame has an unknown spatial relationship with an instrument tracked in a second coordinate frame. The spatial synchronization module 336 is employed to resolve the spatial independence between multiple tracking coordinate frames. Also, the tracking coordinate frames may have unknown spatial relationships to world coordinates frames such as the patient, imaging equipment, or other world coordinate frames.

According to one embodiment, the spatial synchronization module 336 calibrates the coordinate frames for two or more tracking systems 100, 200. The tracking tools (with embedded sensors) 101, 102, 201, 202 connected to each tracking system 100, 200 are used as a pointer to touch a set of fiducials or surface features of a patient or equipment at a location known in a world coordinate frame. By combining the information received from all of the tracked tools in their independent coordinate frames, a spatial transformation matrix (usually called a registration matrix) can be computed using methods known in the art, such as point-based registration methods. The registration matrix may be iteratively computed using the tracking coordinates and the world coordinates at the time of touching the fiducial or surface feature. The registration matrix converts coordinate data from a tracking coordinate frame into corresponding coordinates in a world coordinate frame. Depending on the number of tracked tools, there may be a number of registration matrices to convert their respective data into the fixed world coordinate frame. Medical images and constructed image spaces may have known spatial relationships to the world reference frame as a result of calibration, for example.

After the registration matrices are calculated, they can be saved in the MTI 300. The tracking spaces are thereby stitched together to enable the continuous tracking of multiple tracked tools associated with multiple tracking systems in a single coordinate frame.

In one embodiment, the MTI 300 can send a request to a tracking system 100, 200 to change its measurement data according to a specified registration matrix that is sent by the MTI 300 with a measurement request. The tracking system 100, 200, if capable, will send data transformed from its internal coordinate frame with the registration matrix provided by the MTI 300. This registration matrix can be cached by the tracking device until a new registration matrix is sent with a subsequent request. This capability enables the MTI 300 to delegate coordinate frame synchronization to the tracking systems 100, 200 when possible, and to take responsibility for performing the coordinate frame conversion itself when the tracking systems are not capable of receiving or using the registration matrix.

Figure 5:
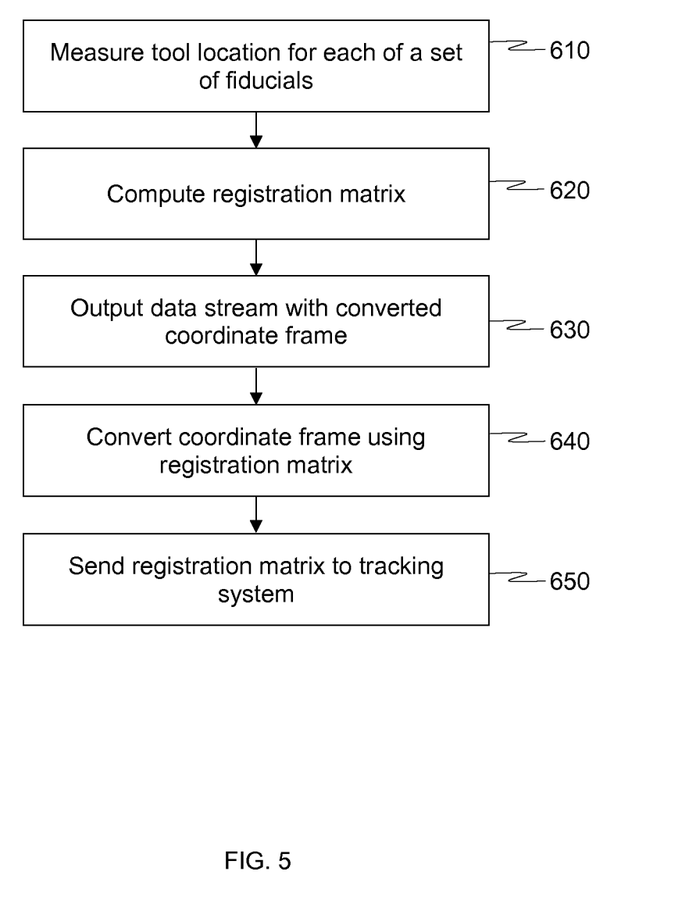
FIG. 5 is a flow diagram of a method for the spatial synchronization according to an embodiment of the present invention.

FIG. 5 is a flow diagram of a method for a spatial synchronization module 336 according to an embodiment of the present invention. The spatial synchronization receives location measurement data for each of a set of fiducials (Step 610). For example, a user may be prompted to touch a tracking tool to a fiducial at a known location in a world frame, such as at a landmark on a patient. The tracking system measures the location of the fiducial in the tracking reference frame and sends it to the spatial synchronization module 336. This step can be repeated for each of a set of fiducials. In an alternative embodiment, grooves or other surface features of equipment or the patient that have known world reference frame locations may be used in place of fiducials. Then, using the tracking reference frame measurements and the world frame locations of the fiducials, the spatial synchronization module 336 calculates a registration matrix to convert the tracking reference frame coordinates to world reference frame coordinates (Step 620) using point-based registration methods. That is, estimated values are iteratively filled into the registration matrix and each reference frame point is converted to a world frame point until the calculated point sufficiently fits the known world coordinates of the fiducials. The spatial synchronization module 336 may use this registration matrix to convert coordinates in the data stream from the tracking system into world coordinates (Step 640), then output the data stream with converted coordinates to the IGI application 422 (Step 650).

In one embodiment, the spatial synchronization module 336 may send the registration matrix to the tracking system (Step 630). If the tracking system is able, it converts the tracking reference frame coordinates to world reference frame coordinates (Step 640). Otherwise the spatial synchronization module 336 does the conversion. The world reference frame should be understood to be a reference frame associated with a real-world feature or structure, such as an imaging system, surgical table, or even the patient.

According to one embodiment, the spatial synchronization module 336 can act as a broker for reference frame dependencies. For example, one tracking system is aware of its transformation matrix between a patient and a fixed coordinate frame in the room (E.g. an imaging system) while a second tracking system is introduced which knows only its relative position to the fixed coordinate frame. The spatial synchronization module 336 can act as a broker, in which the second tracking system announces its presence and its relative coordinate frame. The spatial synchronization module 336 acts as a means to add an additional reference frame (patient frame of reference) to the new device. This may done for example, by sending the registration matrix that registers the fixed coordinate frame in the room to the patient to the second tracking system. The spatial synchronization module 336 could then notify dependent tracking systems when a coordinate frame becomes obsolete, such as when a patient moves. The spatial synchronization module 336 can also initiate or trigger the user to perform a new registration procedure to re-establish the lost reference frame to the dependent tracking systems.

In another embodiment, the spatial synchronization module 336 can allow for sharing pre-procedural information, such as imaging volumes, between tracking systems. For example, a first tracking system has a pre-procedural dataset and knows the link to a current patient coordinate frame and a fixed frame (e.g. x-ray gantry), and a second tracking system is introduced with knowledge of its own coordinate frame and the same fixed frame (e.g. x-ray gantry). The first tracking system can share its pre-procedural dataset with the second tracking system through the spatial synchronization module 336. The second system will be able to track tools relative to the pre-procedural data set using the registration matrix from the common fixed frame to the patient coordinate frame from the first tracking system. When a new tracking system is introduced, the spatial synchronization module 336 can ask the new tracking system for all reference frames and their relationship (i.e. registration matrices) and meta-material and then share them with other tracking systems.

According to one embodiment, the MTI 300 may further comprise a multiplexing unit 350. Each tracking system 100, 200 (often from different vendors) has its own processor and has a specific frame or sample rate at which it makes tool position and orientation measurements. These measurement rates may be different for different tracking systems. The multiplexing unit allows the MTI 300 to run as a synchronous system, with all tracking data temporarily synchronized. According to one embodiment, the multiplexing unit 350 may be realized in a hardware device, such as an integrated circuit with an internal buffer memory. The tracking system continuously streams position and/or orientation measurements to the multiplexing unit 350, which uses a buffer 370 to listen to or store all of the measurements as they arrive. Then, when an internal clock 360 sends a signal to forward measurements to outside IGI applications 422, the multiplexing unit simply selects the most recent measurements for each tracking device from the buffer 370, pairs them up, and forwards them. The multiplexing unit may alternatively overwrite the previous measurement for each tracking device when a new measurement is received for that tracking device.

Alternatively, the multiplexing unit 350 may be a software module that receives and stores measurements in a buffer 370 which may be in the memory 330 or any other memory. The syntax for retrieving and sending the most recent measurements may be expressed as follows:

Repeat {get_trackingDeviceA_info; get_trackingDeviceB_info;}

In some scenarios, such as when the input tracking systems have a large disparity in streaming rate, the user may elect to turn off the "synchronization mode", wherein the multiplexing unit 350 would simply choose to output the tracking streams at the same rate as they arrived. The syntax for a software embodiment for synchronization mode off can be expressed as:

Repeat {get_trackingDeviceA_info;}
Repeat {get_trackingDeviceB_info;}

According to one embodiment, the MTI 300 may further comprise a latency detection and synchronization module 338. The latency for each tracking system will depend on the tracking system and on the conditions under which it is being used—for instance, its internal measurement rate, the number of tools that it is tracking, and the data transmission speed between the tracking system and the computer. Latency is very important when measurements are to be made simultaneously with different tracking systems, e.g. optical and magnetic systems which may have different measurement clocks and latencies.

According to one embodiment, each tracking system 100, 200 can send measurement data with an associated timestamp (the time instance of the measurement acquisition) from the tracking system's own internal clock. However, due to the independence of the tracking systems, there is a need to associate measurements from different tracking systems on one system clock determined by the MTI 300.

The latency detection and synchronization module 338 determine the latency for each tracking system and synchronizes the time measurements on a single system clock. The latency detection and synchronization module 338 requests a new measurement with a timestamp $T_r$ from a tracking device on a tracking system 100. The latency detection and synchronization module 338 records the time of the request $M_{rq}$ from the system clock 360. When the measurement data and tracking system timestamp $T_r$ are received from the tracking system, the latency detection and synchronization module 338 records the measurement data received timestamp $M_{dr}$ from the system clock 360. The latency detection and synchronization module 338 calculates that the tracking system timestamp $T_r$ is equivalent to the average of the two internally generated system timestamps associated with the measurement transaction ($Tr \Leftrightarrow (Mdr+Mrq)/2$). Measurements such as $T_r$ made in the tracking device's clock can be converted into an equivalent timestamp on the MTI's clock thus establishing a relationship between the two clocks—the tracking device's internal clock and the MTI system clock. The latency detection and synchronization module 338 converts the measurement time from the tracking system timestamp to its system clock equivalent, allowing the MTI to temporally synchronize information from multiple tracking devices. It should be noted that this method is immune to slow changes in latency with time, as each measurement received by the MTI from any coordinate reference frame is converted to the MTI's system clock using contemporaneous latency measurements for each transaction.

The latency detection and synchronization module 338 can also synchronize tracking data and image data to a single system clock. This can enable the use of time-dependent imaging data such as different phases of a cardiac cycle to be used with the tracking data for more accurate tracking.

Figure 6:
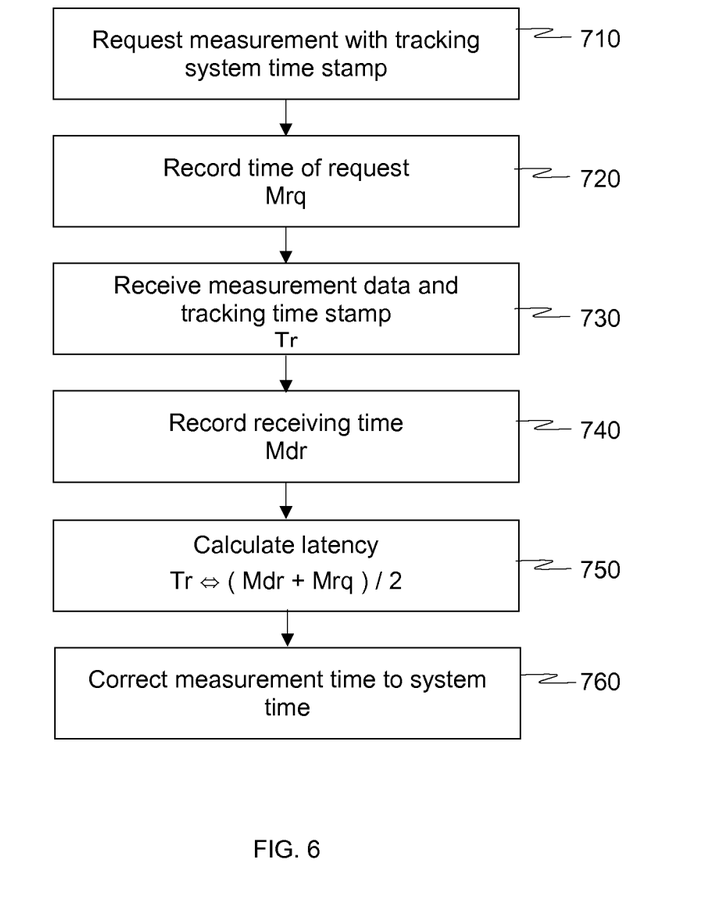
FIG. 6 is a flow diagram of a method for the temporal synchronization according to an embodiment of the present invention.

FIG. 6 is a flow diagram of a method for the temporal synchronization according to an embodiment of the present invention. The latency detection and synchronization module 338 requests a measurement with a tracking system timestamp (Step 710). The latency detection and synchronization module 338 records the time of the request $M_{rq}$ from the MTI clock 360 (Step 720). The latency detection and synchronization module 338 receives the measurement data and tracking system time stamp $T_r$ (Step 730). The latency detection and synchronization module 338 records the time of the data return $M_{dr}$ from the MTI clock 360 (Step 740). The latency detection and synchronization module 338 calculates the latency (Step 750) (($T_r \Leftrightarrow M_{dr}+M_{rq}$)/2), and converts the measurement time $T_r$ to the MTI system time (Step 760).

According to one embodiment, the MTI 300 may further comprise an error handling module 339 that would act as a broker for notifying dependent tracking systems that a tracking system that they depend from has an error. Dependent tracking systems would be tracking systems that use another tracking system for registration as described above. Error types may include communication errors (communication interrupted or dropped), position errors (e.g. ferromagnetic material interference in the case of EM tracking systems), tracked probes are out or near edge of tracked volume, tracking system is turned off or failed.

Since the MTI already has set up a relationship matrix between two or more tracking systems, the error handling module 339 can notify the dependent devices that an error has occurred. Then, new relationships can be constructed and maintained.

Figure 7:
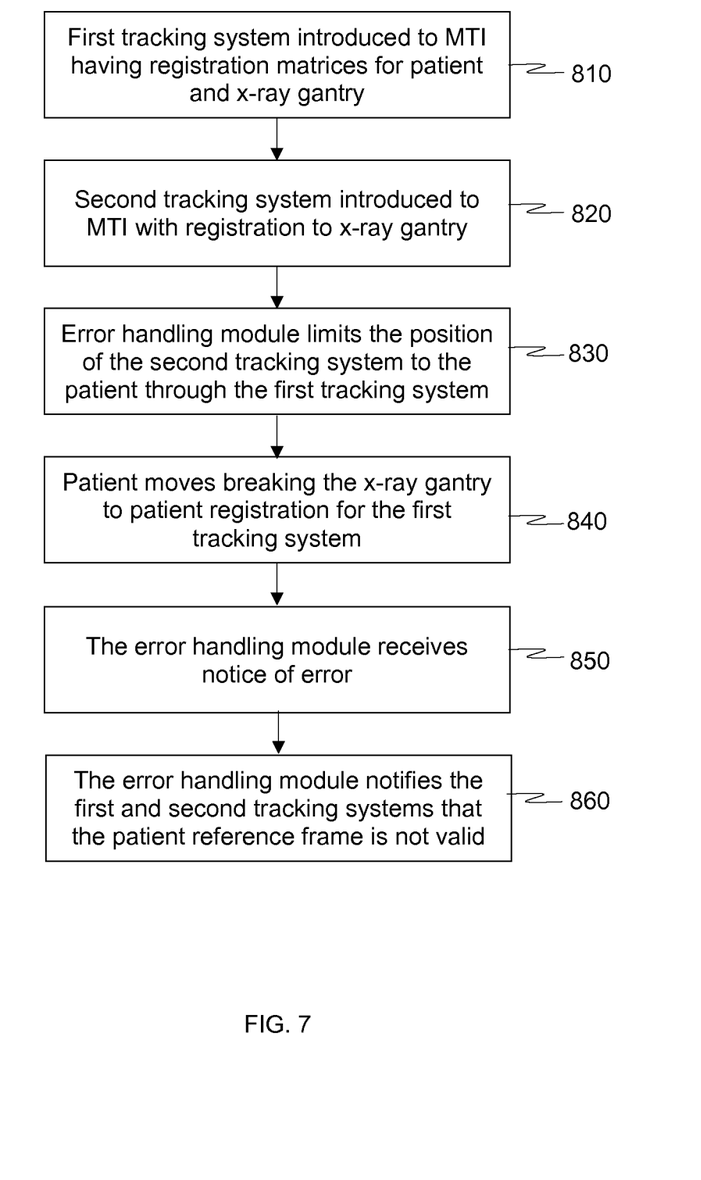
FIG. 7 is a flow diagram of a method for error handling according to an embodiment of the present invention.

FIG. 7 is a process flow for error detection and notification according to an embodiment of the present invention. A first tracking system 100 having registration matrices for a patient frame of reference and an Xray gantry frame of reference is introduced to the MTI 300 (Step 810). A second tracking system 200 having a registration matrix for the Xray gantry is introduced to the MTI 300 (Step 820). The error handling module 339 links the position of the second tracking system 200 to the patient reference frame through the first tracking system 100 storing a dependency relationship indication (Step 830). During an intervention procedure, the patient moves breaking the Xray gantry to patient registration for the first tracking system 100 (Step 840) and an error message is sent to the MTI. The error handling module 339 receives notice of the error (Step 850) and notifies the first and second tracking systems that the patient reference frame is not valid (Step 860). The error handling module 339 can initiate establishing new reference frame dependencies following error notification.

According to one embodiment, temporal synchronization is provided by touching at least one tracked instrument to a fiducial or other reference feature identifiable by the tracking system. In this embodiment, the MTI comprises a clock that provides a uniform temporal reference frame timestamp and the program of instruction detects a touching of the at least one tracking device to a reference feature that is identifiable in an imaging data stream and captures the uniform reference frame timestamp for the touching. The program of instruction also detects the touching in the imaging data stream via analysis of the imaging data stream and captures a timestamp of the imaging stream. Then the program of instruction synchronizes the imaging stream timestamp with the corresponding timestamp from the uniform time reference frame.

The invention can take the form of an entirely hardware embodiment or an embodiment containing both hardware and software elements. In an exemplary embodiment, the invention is implemented in software, which includes but is not limited to firmware, resident software, microcode, etc.

Furthermore, the invention may take the form of a computer program product accessible from a computer-usable or computer-readable medium providing program code for use by or in connection with a computer or any instruction execution system or device. For the purposes of this description, a computer-usable or computer readable medium may be any apparatus that can contain or store the program for use by or in connection with the instruction execution system, apparatus, or device.

The foregoing method may be realized by a program product comprising a machine-readable medium having a machine-executable program of instructions, which when executed by a machine, such as a computer, performs the steps of the method. This program product may be stored on any of a variety of known machine-readable medium, including but not limited to compact discs, floppy discs, USB memory devices, and the like.

The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk an optical disk. Current examples of optical disks include compact disk-read only memory (CD-ROM), compact disk-read/write (CD-R/W) and DVD.

The preceding description and accompanying drawing are intended to be illustrative and not limiting of the invention. The scope of the invention is intended to encompass equivalent variations and configurations to the full extent of the following claims.

What is claimed is:

1. A method for providing a medical tracking interface for communication between at least one interventional tracking tool and an image guided intervention (IGI) application, characterized in the medical tracking interface:
   Receiving tracking data from at least one tracking tool in any one of a plurality of data formats;
   converting the tracking data to a uniform data format; and
   outputting the tracking data in the uniform data format to the IGI application.

2. The method of claim 1, wherein the uniform data format comprises one of: Cartesian coordinates, orientations encoded with rotation axes and angles using quaternions, orientations encoded with rotations using Euler angles, and positions and orientations encoded using a transform matrix, and the positional tracking data comprises any one of: Cartesian coordinates, orientations encoded with rotation axes and angles using quaternions, orientations encoded with rotations using Euler angles, and positions and orientations encoded using a transform matrix.

3. The method of claim 1, wherein the uniform data format comprises spatial alignment of each of the at least one tracking tools to a common world reference frame, and the method further comprises the steps of:
   touching each tracking tool to a plurality of reference features at known locations in the common world reference frame;
   measuring the reference feature locations in the data format of the tracking tool;
   calculating a registration matrix from the reference feature measurements;
   using the reference matrix to align the tracking tool data to world reference frame coordinates of the common world reference frame; and
   outputting the tracking data in the world reference frame coordinates.

4. The method of claim 3, wherein an imaging data is associated with the data format of one of the at least one tracking tools, the method further comprising the step of: sharing the imaging data associated with the data format from the one of the at least one tracking tools to tracked interventional tools associated with a data format for another one of the at least one tracking tools using the registration matrix to align the tracking data of the data format of one of the at least one tracking tools to the tracking data of the data format of the another one of the at least one tracking tools.

5. The method of claim 1, further comprising the steps of: detecting errors in data for one of the at least one tracking tools; and notifying a dependent tracking tool to determine and use new registration matrices.

6. The method of claim 1, wherein the uniform data format comprises a uniform temporal reference frame.

7. The method of claim 6, wherein the at least one tracking tool provides data at any one of a plurality of streaming rates, and the data stream is buffered and output at a uniform streaming rate.

8. The method of claim 7 wherein more than one tracking tool provides data at more than one streaming rate and the data streams are synchronized.

9. The method of claim 1, wherein the uniform data format comprises timestamps with a uniform time reference frame, the method further comprising the steps of:
measuring latency for each of the at least one tracking tools; and
converting a tracking device timestamp to an equivalent uniform interface timestamp using the measured latency.

10. The method of claim 1, wherein the uniform data format comprises timestamps with a uniform time reference frame, the method further comprising the steps of:
collecting physiological monitoring data; and
synchronizing the tracking data with the physiological monitoring data.

11. The method of claim 1, wherein the uniform data format comprises timestamps with a uniform time reference frame, further comprising the steps of:
touching at least one tracking tool to a reference feature that is identifiable in an imaging data stream;
detecting the touching in the imaging data stream via analysis of the imaging data stream and capturing a timestamp of the imaging stream;
synchronizing the imaging data stream timestamp with a corresponding timestamp from the uniform time reference frame.

12. A medical tracking interface, comprising:
a processor;
a memory operably connected to the processor; and
a program of instruction stored on the memory and executed by the processor to convert tracking data from an interventional tool in any of a plurality of data formats to a uniform data format and output the tracking data to an image guided intervention application in the uniform data format.

13. The medical tracking interface of claim 12, further comprising a multiplexer, wherein the multiplexer temporally aligns each of the at least one interventional tools to a medical tracking interface reference.

14. A computer program product comprising a non-transient computer readable storage device having encoded thereon a computer executable program of instruction, comprising:
program instructions for receiving data from at least one tracking tool in any one of a plurality of data formats;
program instructions for converting the data to a uniform data format; and
program instructions for outputting the data in the uniform data format to an image guided intervention application.

* * * * *